United States Patent
Campion et al.

(10) Patent No.: US 9,179,958 B2
(45) Date of Patent: Nov. 10, 2015

(54) DISPENSING INSTRUMENT

(71) Applicant: ApaTech LTD, Elstree, Hertfordshire (GB)

(72) Inventors: Charles Campion, Elstree (GB); Thomas Buckland, Elstree (GB); Paul Kearsley, Elstree (GB)

(73) Assignee: ApaTech LTD., Hertfordshire (GB)

( * ) Notice: Subject to any disclaimer, the term of this patent is extended or adjusted under 35 U.S.C. 154(b) by 397 days.

(21) Appl. No.: 13/861,931

(22) Filed: Apr. 12, 2013

(65) Prior Publication Data

US 2013/0226188 A1  Aug. 29, 2013

Related U.S. Application Data

(63) Continuation of application No. 12/393,318, filed on Feb. 26, 2009, now Pat. No. 8,439,930.

(30) Foreign Application Priority Data

Jun. 23, 2008 (GB) .................................. 0811512.3

(51) Int. Cl.
*A61B 17/88* (2006.01)
*A61F 2/46* (2006.01)
*A61B 17/29* (2006.01)

(52) U.S. Cl.
CPC .......... *A61B 17/8822* (2013.01); *A61B 17/8816* (2013.01); *A61F 2/4601* (2013.01); *A61B 2017/2923* (2013.01); *A61F 2002/4627* (2013.01)

(58) Field of Classification Search
CPC .......... A61F 2/4601; A61F 2002/4627; A61B 2017/2923

USPC ....... 88/54; 606/53, 86 R, 92, 93, 94; 42/138; 254/206, 217, 223, 235, 237, 247, 306, 254/320; 604/19, 48, 93.01, 181, 187, 207, 604/208, 209, 220, 223, 221, 224; 222/325–327, 386, 391
See application file for complete search history.

(56) References Cited

U.S. PATENT DOCUMENTS

| 2,233,587 | A | * | 3/1941 | Crewe ............................. 74/169 |
| 4,264,305 | A | | 4/1981 | Rasmussen et al. |
| 4,569,662 | A | | 2/1986 | Dragan |
| 4,576,591 | A | | 3/1986 | Kaye et al. |
| 4,994,065 | A | | 2/1991 | Gibbs et al. |
| 5,435,645 | A | | 7/1995 | Faccioli et al. |
| 5,893,488 | A | | 4/1999 | Hoag et al. |

(Continued)

FOREIGN PATENT DOCUMENTS

GB   2445421   7/2008

*Primary Examiner* — David Bates
*Assistant Examiner* — Samuel Hanna
(74) *Attorney, Agent, or Firm* — Greer, Burns & Crain, Ltd.

(57) ABSTRACT

A delivery device for semi-solid implantable material such as synthetic bone graft substitutes. The device includes a handle, a cylinder extending from the handle and having an outlet at its distal end. A piston is operated by a trigger and is slidable within the cylinder to displace the material from the cylinder. The cylinder has a substantially constant inner diameter along its entire length such that the outlet has substantially the same inner diameter as the rest of the cylinder. When the trigger is fully depressed, a ratchet mechanism is disengaged allowing the piston to be pulled back to a starting position.

11 Claims, 4 Drawing Sheets

(56) References Cited

U.S. PATENT DOCUMENTS

| | | |
|---|---|---|
| 6,149,655 A | 11/2000 | Constantz et al. |
| 6,599,272 B1 | 7/2003 | Hjertman et al. |
| 2002/0092871 A1 | 7/2002 | Rickard et al. |
| 2004/0006348 A1 | 1/2004 | Peterson et al. |
| 2007/0093790 A1* | 4/2007 | Downey et al. ............ 606/1 |
| 2007/0233146 A1 | 10/2007 | Henniges et al. |
| 2008/0290115 A1 | 11/2008 | Amron |

\* cited by examiner

DISPENSING INSTRUMENT

RELATED APPLICATION

This application is a continuation of U.S. Ser. No. 12/393,318, filed Feb. 26, 2009.

BACKGROUND

The present invention relates to a dispensing instrument. The invention has been specifically designed for the dispensing of a semi-solid implantable material such as synthetic bone graft substitutes; demineralised bone matrices; bone graft extenders; calcium phosphate cements; polymethylmethacrylate cements; bone cements; dental cements. However, the dispenser may be used to dispense a variety of semi-solid materials or viscous liquids.

Known delivery systems for semi-solid materials in medicine have traditionally been based on two-part or three-part syringes where the dispensing of the material from the dispensing part is achieved by the user applied force transmitted directly through a plunger or through a separate displacement piston. This has limitations. For example, the maximum force generated by the user is relatively low due to the lack of mechanical advantage provided by the dispensers.

More complex systems for delivery of high viscosity liquids are known in the prior art.

One such product is the well-known mastic gun. This has a cradle-like portion arranged to receive a cartridge of high viscosity liquid, such as a filler or sealant. The device has a handle with a squeezable trigger. The trigger is pivotally mounted about an axis adjacent to the cartridge. One end of the trigger is squeezed by a user and the opposite end pushes on a piston within the cartridge. A spring biases the trigger so that, upon its release, it returns to its starting position allowing further movement of the trigger to selectively depress the piston and dispense more material. A spring loaded latch engages with a piston rod to prevent retraction of the piston rod during operation. When the cartridge is empty, the spring loaded latch is depressed and this allows the piston rod to be pulled out of the cartridge. In view of the cradle-like nature of the design, and also to ensure accurate dispensing of the material, the cartridge is provided with a nozzle through which the material is dispensed.

Such an arrangement is impractical for the dispensing of semi-solid implantable materials as the nozzle design generates a significant amount of latent hydraulic pressure in the liquid during dispensing which can cause an overrun of the material dispensed after the pressure on the handle has been relieved. The nozzle is also prone to clogging, particularly were it to be used with a semi-solid material. Similar devices are known in the medical field. A cement injection gun sold by Stryker®, and also by Orthovita® under the Cortoss® brand.

SUMMARY

According to the present invention, there is provided a delivery device, the device comprising a handle, a cylinder extending from the handle and having an outlet at its distal end, a piston slidable within the cylinder to displace the material from the cylinder, a trigger pivotally mounted on the handle which is manually operable by a user, the trigger being coupled to the piston such that the operation of the trigger causes a movement of the piston towards the outlet of the cylinder, wherein the cylinder has a substantially constant inner diameter along its entire length such that the outlet has substantially the same inner diameter as the rest of the cylinder.

By providing a dispensing device with a substantially constant diameter portion for the cylinder, the problems associated with a nozzle having a relatively small dimension as compared to the rest of the cylinder are avoided. The requirement for a substantially constant inner diameter covers cylinders with an entirely constant inner diameter and also those having a part with a slight taper which is insignificant in the sense that it does not interfere with the flow of material from the cylinder. This should be contrasted with the abrupt transition which is associated with the nozzles of the prior art.

Although the device has been designed specifically for use with semi-solid implantable materials, it can readily be used with any semi-solid or viscous material.

The cylinder is preferably a component which is removable from the handle. This may be mounted using a similar cradle arrangement to that associated with the known mastic gun. This would require an outwardly projecting mounting flange to be provided at the distal end of the cylinder to be supported in the cradle. However, preferably, the cylinder is mountable to the handle only at the proximal end of the cylinder. This ensures that only the cylinder and no part of the mounting protrudes distally from the handle. This is beneficial in an implanting device as the reusable part of the device can be kept out of contact with the tissues of the body during surgery in deep tissues. The cylinder can be supplied as a pre-filled part in sterile packaging.

Also, the device can readily accommodate cylinders of different diameters and lengths.

The sub-assembly forms an independent aspect of the present invention which, in its broadest sense, comprises a sub-assembly of a cylinder having a constant inner diameter along its entire length such that the outlet has the same inner diameter as the rest of the cylinder filled with a semi-solid implantable material having a removable closure element at its distal end and, at its proximal end, having a releasable attachment mechanism for attachment to a dispensing device.

The attachment mechanism may be any form of releasable attachment mechanism such as a bayonet, screw-thread or detent mechanism.

The closure member at the distal end may be a plug which fits within the cylinder, but is preferably a cap which fits over the end of the cylinder as this provides additional protection against accidental contamination of the tip of the cylinder as the device is prepared for use.

The cylinder is also preferably closed at its proximal end. The closure may be a piston member which, in use, is advanced along the cylinder by a piston rod in the handle. Alternatively, the proximal end may be closed by a removable plug or cap.

The handle may be of conventional design such as that used in known mastic guns, in which the trigger is pivoted about an axis which is adjacent to the cylinder. In this case, the end of the trigger furthest from the cylinder is pulled back towards the main body of the handle causing the trigger to rotate about the pivot. The opposite end of the trigger moves forward thereby pushing a piston rod, and hence the piston, along the cylinder. Although such a design provides a mechanical advantage allowing the user to apply a greater force, it does have the drawback that, in its initial position, the trigger is spaced a considerable distance from the main body of the handle meaning that, in order to operate the device, the user's hand is initially at full stretch. This can be somewhat awkward for the user to manipulate, thereby limiting the force which can be applied and/or affecting the stability of the device in use, particularly, for those with smaller hands.

Therefore, preferably, the trigger of the present invention is pivotally mounted to the main body of the handle at a point remote from the cylinder, the end of the trigger adjacent to the cylinder is provided with teeth, a toothed wheel is rotatably mounted in the handle adjacent to the teeth on the trigger and is positioned so that depression of the trigger causes rotation of the wheel, the wheel being operatively connected to a slider within the main body of the handle provided with teeth which engage with the teeth of the wheel such that rotation of the wheel advances the slider and hence the piston. Pivoting the trigger in this way and using the gear wheel to transmit this motion to the piston, removes the need for the distal end of the trigger to initially be positioned a significant distance from the handle. This results in a device which is simpler to operate than the prior art.

The device may rely upon a spring loaded latch such as that used in the prior art in order to prevent the piston rod from being retracted when the trigger is released. However, preferably, the device is provided with a ratchet mechanism to prevent retraction of the piston when the trigger is released.

The ratchet mechanism preferably comprises a spring loaded pawl in the handle which engages with a set of teeth in a piston rod attached to the piston, the spring loaded pawl being disengaged from the teeth when the trigger is fully depressed and arranged to be re-set upon release of the trigger. Thus, when the trigger is fully depressed, but is yet to be released, the pawl is disengaged from the teeth allowing the piston rod to be withdrawn from the cylinder. This is useful as, once the user has finished dispensing from a particular cylinder, they simply need to hold the trigger in the closed position and pull the rod out of the cylinder. This is a simpler process than the prior art which additionally requires the manipulation of a separate latch. This can be awkward in a surgical procedure where it is desirable to provide a device which allows the user to complete the procedure using as few hands as possible.

This forms a second aspect of the invention which can be defined in the broadest sense, a delivery device comprising a handle, a cylinder extending from the handle and having an outlet at its distal end, a piston slidable within the cylinder to displace the material from the cylinder, a trigger pivotally mounted on the handle which is manually operable by a user, the trigger being coupled to the piston such that the operation of the trigger causes a movement of the piston towards the outlet of the cylinder and a ratchet mechanism to prevent retraction of the piston when the trigger is released, wherein the ratchet mechanism comprises a spring loaded pawl in the handle which engages with a set of teeth in a piston rod attached to the piston, the spring loaded pawl being disengaged from the teeth when the trigger is fully depressed and arranged to be re-set upon release of the trigger.

BRIEF DESCRIPTION OF THE DRAWINGS

An example of a device in accordance with the present invention will now be described with reference to the accompanying drawings, in which.

DETAILED DESCRIPTION

The device comprises a permanent handle portion 1 in which a cylinder 2 is releasably attached via a bayonet mounting 3 as will be described in more detail below.

The cylinder 2 is preferably a flexible polycarbonate tube which is transparent to allow easy visualisation of the contents. The wall thickness is 0.6-0.7 mm. The outer diameter should be no greater than 8 mm and the fill volume should be no less than 7.5 ml. The tube has a circular cross-section of uniform cross-section throughout. An alternative cartridge may also be provided with an outside diameter of no greater than 5 mm to allow access into small voids and defects in the human body. In the device in the preferred example, the cartridge is 218 mm long, but any other suitable lengths may be employed.

Figure 1:
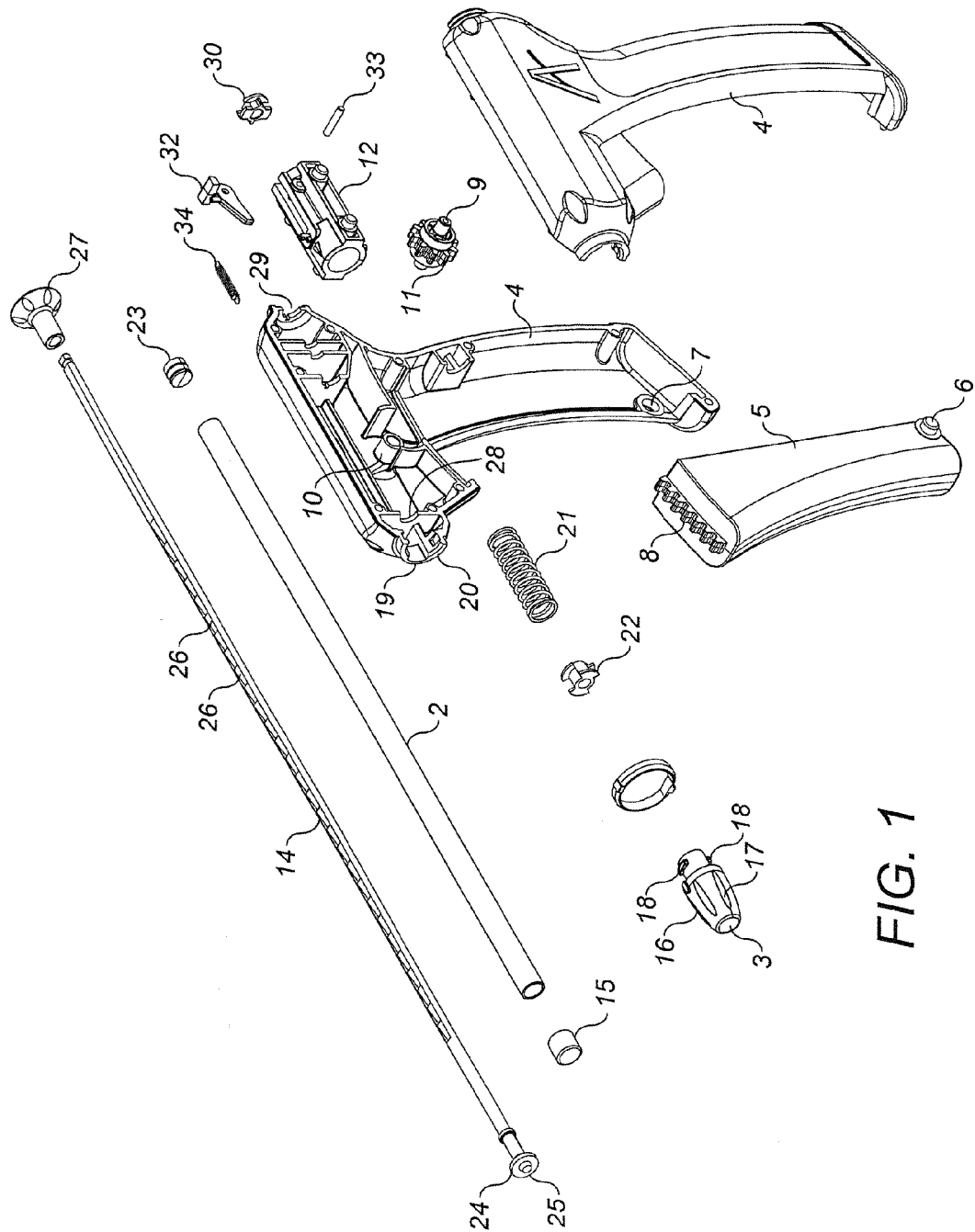
FIG. 1 is an exploded perspective view of the device including the cylinder, piston and piston rod.

The handle portion 1 comprises a housing 4 made up of a two-part moulding as shown in FIG. 1. A trigger 5 is mounted between the two parts of the housing 4. The lower end of the trigger 5 is provided with a pivot projection 6 as shown in FIG. 1 with a similar pivot projection 6 on the opposite side of the handle. These pivot projections 6 fit into a pair of corresponding pivot recesses 7, one of which is shown in FIG. 1, and the other of which will be provided in the other housing 4 in a position to receive the pivot projection 6. This allows the trigger 5 to pivot from an unactuated position shown in FIG. 2 to an actuated position shown in FIG. 3 to actuate the device.

At the top end of the trigger, a plurality of trigger gear teeth 8 are arranged along an arcuate path centred on the pivot projection 6.

A toothed wheel 9 is rotatably mounted in a boss 10 in the housing 4 of the handle 1, such that the toothed wheel 9 is positioned within the two parts of the housing 4 when the handle 1 is assembled. The toothed wheel 9 has wheel teeth 11 which mesh with the trigger gear teeth 8.

A cartridge 12 is slidably mounted within the upper part of the housing 4. The cartridge 12 is provided with cartridge gear teeth 13 which engage with the wheel teeth 11 of the toothed wheel 9 such that the cartridge is advanced forwards within the housing 4 as the trigger 5 is depressed.

Advancing the cartridge causes a piston rod 14 to be advanced along cylinder 2 as set out below.

The material to be dispensed, in this case a semi-solid implantable material, is contained in the cylinder 2. The device is particularly designed to dispense a semi-solid with a high solid content, namely one with a packing efficiency of greater than 90%, and preferably greater than 92.5%, (i.e., greater than 90% or 92.5% of the composite material contains solid particles with the remainder of the volume being a carrier material). The solid particles may, for example, be porous ceramic, such as porous hydroxyapatite and tricalcium phosphate formulations; predominantly structural particulate organic allograft materials, such as non-demineralized bone chips; or polymer beads, such as porous polyethylene.

Figure 4:
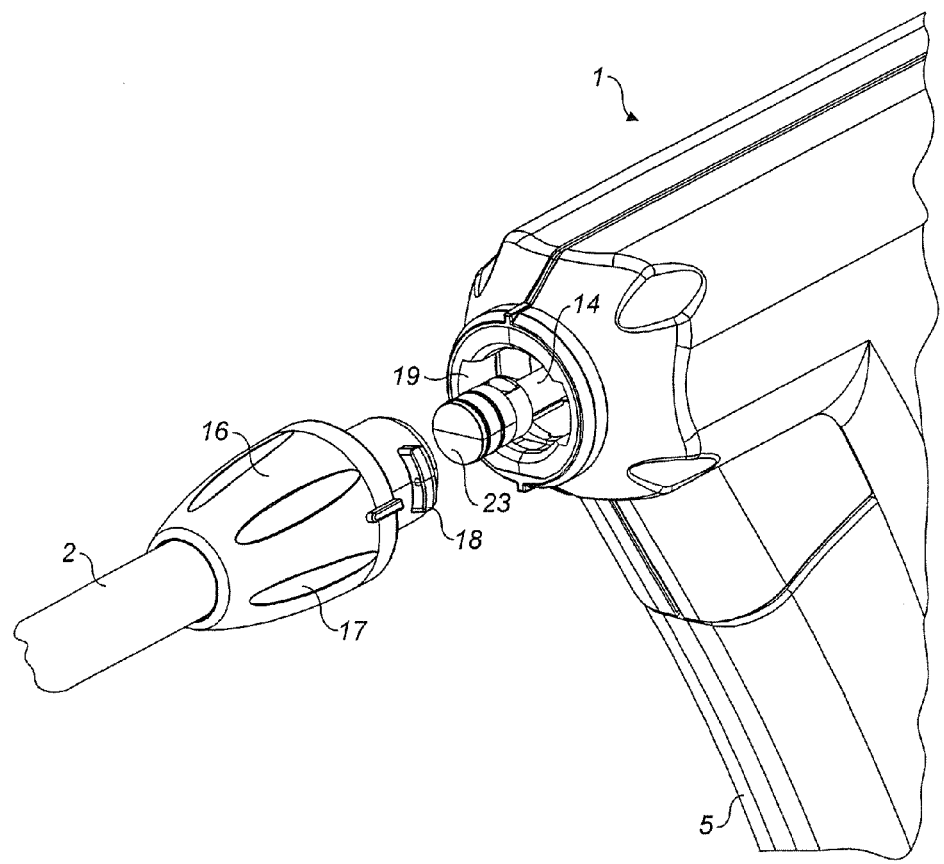
FIG. 4 is an exploded perspective view of the device showing the attachment between the handle and cylinder.

At its distal end, the tube is closed by a cap 15. The proximal end of the tube is fitted to a bayonet mounting 3 in which it may be a friction fit, or may be bonded in place so that it is sealed with respect to the bayonet. As shown in FIG. 4, the bayonet 3 has a distal portion 16 with a plurality of recesses 17 which allow it to be easily gripped. The proximal end of the bayonet has a pair of lugs 18 which pass through corresponding openings 19 on the front of the handle portion 1. The bayonet is then rotated so as to engage the lugs 18 with an inwardly facing surface 20 at the front of the handle portion 1.

In order to further secure the bayonet fixing, a return spring 21 which is arranged to return the cartridge 12 as will be described in more detail below is also arranged to bear against a support ring 22 which itself bears against the distal face of the bayonet 16, thereby urging the flanges 18 into contact with the surface 20.

The piston 23 may be provided within the bayonet 16 such that, in use, it can be picked up by the advancing piston rod 14. Alternatively, as shown in FIG. 4, the piston 23 is an integral part of the piston rod 14. In this case, the cylinder 2 can be provided with a separate plug (not shown) at the proximal end in order to retain the material within the cylinder during storage and transportation. Such a plug would be inserted in the proximal end of the tube and removed prior to attachment to the handle portion 1.

A combination of the cylinder 2, implantable material, bayonet 3, cap 15 and optionally the piston 23 or plug are intended to be supplied as a disposable component. In use, when the material of a cylinder has been expelled, the user simply has to withdraw the piston rod as described below, undo the bayonet 3 removing this together with the cylinder and replace it with the new full cylinder if necessary. It will be appreciated that the device can readily be used with cylinders having different diameters. Each can be supplied with its own bayonet as all that is required is that the bayonet mounting be compatible with the mounting on the front of the device. In the case where the piston is integral with the tube, there is no need to separately change the piston. If this is not the case, an additional step will be required, namely to fit a new piston 23 to the piston rod 14 which has the appropriate diameter for the new tube.

Finally, the manner in which the piston 23 is advanced along the cylinder will be described.

Figure 2:
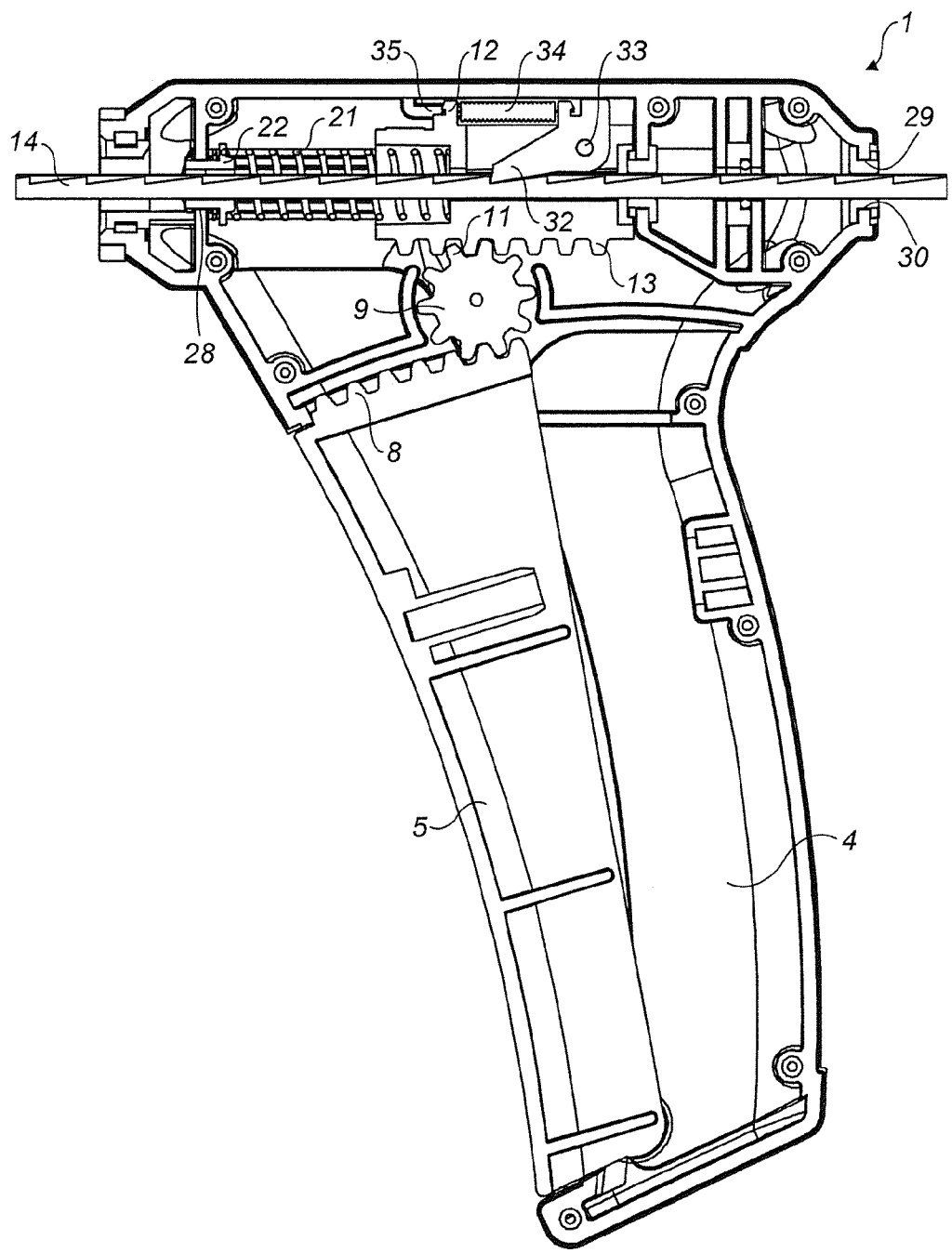
FIG. 2 is a cross-section of the device in an unactuated configuration.
Figure 3:
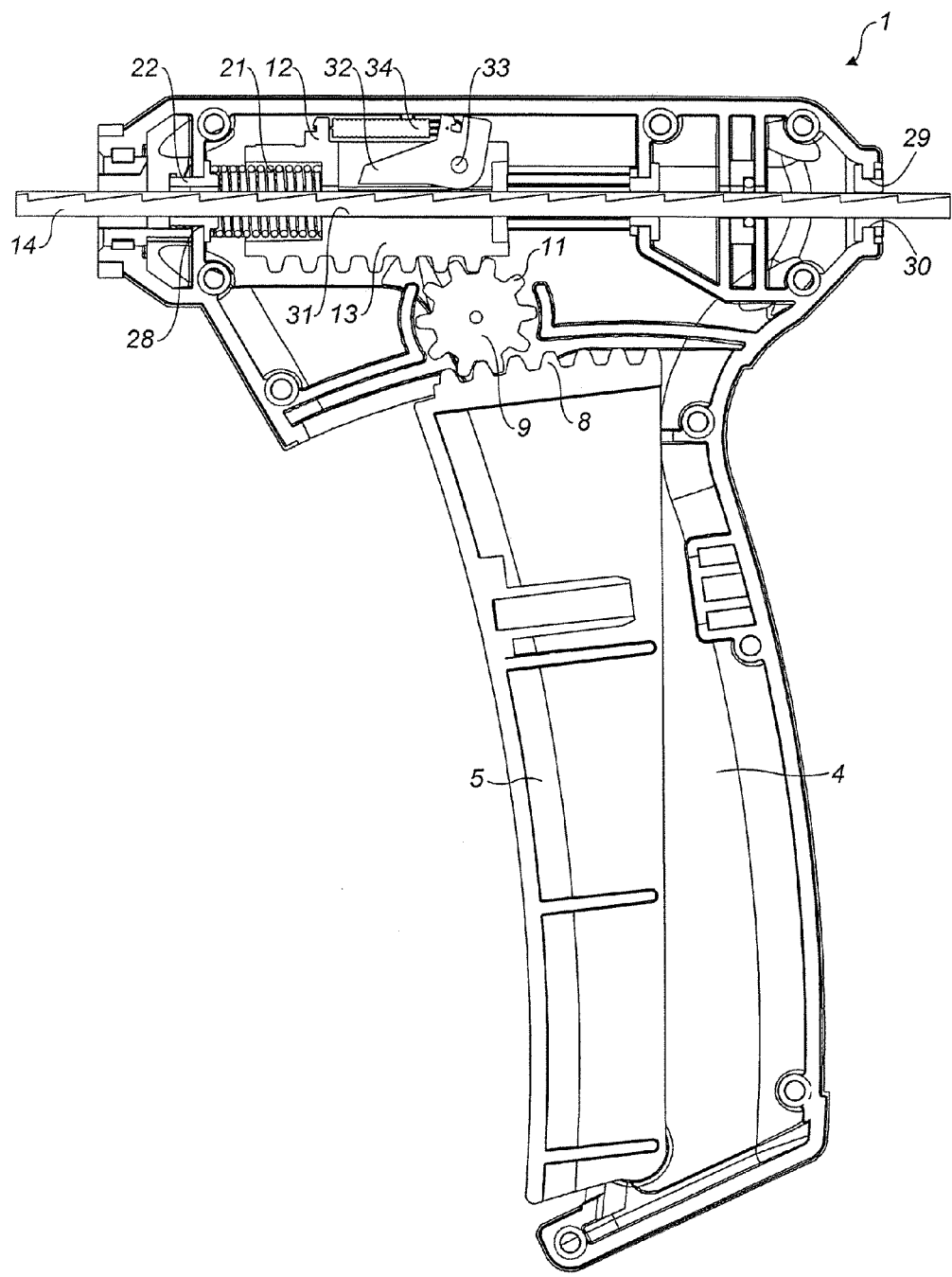
FIG. 3 is a view similar to FIG. 2 with the device in an actuated configuration.

The piston rod is best shown in FIGS. 1 to 3. At its distal end it is provided with a flange 24 and end projection 25 which are designed to pick up the piston 23. Alternatively, the piston may be already in place on the distal end of the piston rod 14. Along its upper surface are a plurality of teeth 26 having a shark tooth configuration with a long gently inclined face in the direction facing the distal end and a short steep face facing the proximal end. A pull stop 27 is provided at the proximal end of the piston rod 14 which is manually grasped to retract the piston rod as described below.

The handle portion 1 is provided with a front opening 28 and a rear opening 29. The support ring 22 is positioned within the front opening 28 and provides a forward support for the piston rod 14 while a similar rear support ring 30 is provided in the rear opening 29 to support the piston rod 14. Thus, the piston rod passes through the rear support ring 30, a central bore 31 in the cartridge 12, the return spring 21, the front support ring 22 and into the bayonet 16 terminating at piston 23.

The return spring 21 acts between the cartridge 12 and the support ring 22 to urge the cartridge 12 to the right as shown in FIG. 2. A pawl 32 is pivotally mounted within the cartridge 12 on a support pin 33. A pawl spring 34 urges the pawl 32 in an anti-clockwise direction about the pivot pin 31 so that the tip of the pawl is urged into its lowermost position. Thus, when the trigger 5 advances the carriage 12 to the left, the spring 34 ensures good engagement between the pawl 32 and the teeth 26 thereby pushing the rod 14 to the left. This also compresses the return spring.

A stop 35 projects downwardly from the top of the housing as shown in FIG. 2. When the trigger 5 is fully depressed to the position shown in FIG. 3, this stop bears against the top of the pawl 32 overcoming the force of the spring 34 and rotating the pawl 32 clockwise to the position shown in FIG. 3. At this point, the user has two options. Firstly, they can release the trigger 5, thereby returning the carriage 12 to its starting position under the action of return spring 21, during which time the pawl 32 rides over two teeth and returns to the starting position shown in FIG. 2. Alternatively, if the user has expelled all of the material that they require from the cylinder 2 without releasing the trigger 5, they may grasp the pull stop 27 and pull the piston rod 14 out of the cylinder. They can then either fit a new cylinder 2 as set out above, or this simply concludes the implanting process.

What is claimed is:

1. A delivery device comprising:
   a handle having a first end and a second end disposed generally opposite each other;
   a cylinder extending from the first end of the handle and having an outlet at its distal end;
   a piston slidable within the cylinder for displacing a material from the cylinder;
   a trigger having a lower end and a top end, the lower end being pivotally mounted on the second end of the handle and the top end being positioned adjacent the first end of the handle, the handle being manually operable by a user such that the operation of the trigger causes a movement of the piston towards the outlet of the cylinder;
   a toothed wheel rotatably mounted and positioned in the handle between the top end of the trigger and the piston such that depression of the trigger causes rotation of the toothed wheel to move the piston towards the outlet of the cylinder;
   a ratchet mechanism for preventing retraction of the piston when the trigger is released; and
   wherein the ratchet mechanism comprises a spring loaded pawl in the handle which engages with a set of teeth in a piston rod attached to the piston,
   wherein the spring loaded pawl is disengaged from the teeth by the trigger being fully depressed, thereby allowing the piston rod to be removed from the cylinder, and
   wherein the spring loaded pawl is re-set into engagement with the teeth by the trigger being released, thereby preventing retraction of the piston rod, and wherein the toothed wheel and the spring loaded pawl are disposed on opposite sides of the piston rod.

2. A delivery device comprising:
   a handle having a first end and a second end disposed generally opposite each other;
   a cylinder extending from the first end of the handle and having an outlet at its distal end;
   a piston slidable within the cylinder for displacing the material from the cylinder;
   a trigger having a lower end pivotally mounted on the second end of the handle, the handle being manually operable by a user, the trigger further comprising a top end positioned adjacent the first end of the handle, the top end having first teeth engaging second teeth of a toothed wheel rotatably mounted and positioned in the handle such that depression of at least the top end of the trigger causes rotation of the toothed wheel; and
   wherein the toothed wheel is operatively coupled to a slider having third teeth disposed within the handle, a same set of the second teeth directly and simultaneously engaging both the first and third teeth, such that rotation of the wheel initiated by the depression of the trigger advances the slider and causes a movement of the piston towards the outlet of the cylinder, and the depression of the trigger is in a first direction, and due to action of the toothed wheel, a resulting simultaneous movement of the slider is in a second, opposite direction; and wherein when the trigger is partially depressed, the device is constructed and arranged such that the piston is moved in a distal direction towards the outlet of the cylinder, and when the trigger is fully depressed, the piston is removable proximally, and slidably from the cylinder and the handle.

3. The delivery device according to claim 2, wherein the first direction and the second, opposite direction form a straight angle of approximately 180°.

4. The delivery device according to claim 2, further comprising a ratchet mechanism for preventing retraction of the piston when the trigger is released; and a spring loaded pawl in the handle for engaging with fourth teeth on a piston rod attached to the piston, the spring loaded pawl being disengaged from the fourth teeth by the trigger being fully depressed, thereby allowing the piston rod to be removed from the cylinder.

5. The delivery device according to claim 4, further comprising a pull stop at a proximal end of the piston rod, which is manually grasped by the user to retract the piston rod.

6. The delivery device according to claim 4, wherein the trigger and the spring loaded pawl are disposed on opposite sides of the piston rod.

7. The delivery device according to claim 4, further comprising a return spring that directly biases the slider away from the outlet, wherein the piston rod passes through the return spring and the slider.

8. The delivery device according to claim 4, wherein the first teeth of the trigger are arranged along an arcuate path centered on a pivot projection of the second end of the handle.

9. The delivery device according to claim 4, further comprising a pawl spring that urges a top portion of the spring loaded pawl, thereby rotating the spring loaded pawl about a pivot pin such that a tip portion of the spring loaded pawl is urged into a lowermost position for locking the piston rod.

10. The delivery device according to claim 9, further comprising a stop that bears against the top portion of the spring loaded pawl such that the stop urges the spring loaded pawl to rotate about the pivot pin for releasing the piston rod.

11. The delivery device according to claim 9, wherein the spring loaded pawl is disengaged from the fourth teeth when the trigger is full depressed and arranged to be re-set upon release of the trigger.

\* \* \* \* \*